United States Patent [19]

Ganz et al.

[11] Patent Number: 5,229,838
[45] Date of Patent: Jul. 20, 1993

[54] PHOTODETECTOR AMPLITUDE LINEARITY

[75] Inventors: Alan M. Ganz, Trumbull; David H. Tracy, Norwalk, both of Conn.

[73] Assignee: The Perkin-Elmer Corporation, Norwalk, Conn.

[21] Appl. No.: 823,631

[22] Filed: Jan. 21, 1992

[51] Int. Cl.$^5$ .............................................. G01J 3/02
[52] U.S. Cl. .................................. 356/328; 250/252.1
[58] Field of Search ............... 356/300, 308, 319, 325, 356/323, 326, 328, 218, 222, 225; 250/252.1 A

[56] References Cited

PUBLICATIONS

"Automated High Precision Variable Aperture For Spectrophotometer Linearity Testing" by J. C. Zwinkels and D. S. Gignac, Applied Optics, 30, 1678–1687 (May 1, 1991).

Primary Examiner—F. L. Evans
Attorney, Agent, or Firm—H. S. Ingham; E. T. Grimes; J. R. Wahl

[57] ABSTRACT

To calibrate a photodetector, a rotating disk with a slot is disposed in a light beam with decreasing speed from a defined maximum rotational speed to a defined minimum speed, while magnitudes and times of signals are read out and stored. Vernier pairs of signals occur in adjacent readout intervals, and non-vernier signals exclude the verniers. Readout times for verniers are used to estimate a preliminary function of rotations versus time. From the function are estimated an occurrence time for each pair and period of disk rotation at the time. Vernier fraction is the ratio of one signal in the pair to the sum of the pair. A time offset is the product of vernier fraction, slot fraction of the disk and the estimated period. Occurrence times corrected with the time offset are utilized to fit a corrected function of disk rotations versus time. Points of time for the non-vernier signals are determined from the corrected function, each point corresponding to disk rotations to a corresponding non-vernier signal. These points of time are employed with corresponding signals for linearly calibrating the photodetector.

17 Claims, 6 Drawing Sheets

PHOTODETECTOR AMPLITUDE LINEARITY

This invention relates to photometric devices and particularly to determination of linearity of a photodetector in such a device, the linearity being with respect to amount of light received during the readout period of the photodetector.

BACKGROUND OF THE INVENTION

Photodetectors are used in a variety of instruments where amount of light is to be measured. One class of detectors provides periodic readouts of light accumulated during sequential time intervals. These detectors are well known and generally are solid state, based on the principles of charge generation upon the incidence of radiation on a surface such as doped silicon. To provide image or spectral resolution the surface is divided into pixel areas. The accumulations and readouts of signals from the pixels are effected through the transfer of charges from the pixels, with readouts repetitively cycled through the pixels.

The solid state photodetectors are quite accurate in linearity of signal strength versus amount of light collected in a readout period. The amount of light may be variously defined as the total number of photons collected, or the light intensity integrated over the period. However, linearity is not perfect and calibration is necessary for levels of precision needed in some instruments, for example an absorption spectrophotometer for analysis of liquids.

Calibrations have been effected in various ways such as by varying intensity of a source lamp, but this may not provide the precision required. A conventional method of calibration is to vary the readout period of the detector. However, changing the readout period of self scanned array detectors may in itself cause changes in detector responsivity.

Another method utilizes multiple apertures, allowing the light intensity to be measured through each one and then in combination. By taking the ratio of the combined intensity to the sum of the individual ones, a degree of nonlinearity can be determined. A newly implemented method based on a similar scheme is disclosed in "Automated High Precision Variable Aperture for Spectrophotometer Linearity Testing" by J.C. Zwinkels and D.S. Gignac, Applied Optics, 30, 1678–1687 (May 1, 1991). This requires high precision PZT motors driven by a dedicated controller under microcomputer direction.

SUMMARY OF THE INVENTION

An object of the present invention is to determine linearity of a photodetector of the type that has sequential readouts of signals, each signal correlating with amount of light received during a corresponding readout interval, each readout having a time of readout, and all readout intervals being equal to a predetermined readout period. Another object is to provide a photometric instrument having a precisely calibrated photodetector.

The foregoing and other objects are achieved by a method in which a train of light pulses is directed to the photodetector, the light pulses having equal intensity and a variable pulse period between successive pulses, and each light pulse having a variable pulse width equal to a constant fraction of pulse period. The constant fraction and a maximum pulse period are selected cooperatively so that each pulse width is not greater than the readout period. A minimum pulse period is selected so as to be not less than two times the readout period. The pulse period is changed smoothly between the maximum pulse period and the minimum pulse period, while sequential signals from the photodetector and corresponding times of readout are read out and stored.

A set of vernier pairs of signals are identified as those pairs of signals occurring in adjacent readout intervals, and a set of non-vernier signals excluding the vernier pairs are established. Occurrence times are ascertained for the vernier pairs, as are a corresponding total number of light pulses to each occurrence time. The occurrence times are utilized to fit an occurrence function of total number of light pulses versus time. The non-vernier signals are correlated to the occurrence function so as to effect a plot of the non-vernier signals versus pulse period as a measure of linearity of the photodetector.

Preferably, the correlating to the occurrence function is effected as follows: From the occurrence curve, points of time are determined for the non-vernier signals and, also, a further curve is computed representative of pulse period versus time. From the further curve a corresponding pulse period is identified for each point of time and thereby for each corresponding non-vernier signal. The non-vernier signals are then plotted versus pulse period.

The objects also are achieved with a precision photometric instrument comprising the photodetector and light means for directing a train of light pulses to the photodetector, the light pulses having equal intensity and a variable pulse period between successive pulses, and each light pulse having a variable pulse width equal to a constant fraction of pulse period. The instrument also comprises storing means for storing sequential signals from the photodetector and corresponding times of readout, and changing means for smoothly changing the pulse period between a maximum pulse period and a minimum pulse period so as effect a series of sequential signals, the minimum pulse period being not less than two times the readout period, and the maximum pulse period and the constant fraction cooperatively being such that each pulse width is not greater than the readout period.

The instrument further comprises means for identifying a set of vernier pairs of signals as those signals occurring in adjacent readout intervals, establishing a set of non-vernier signals excluding the vernier pairs, ascertaining occurrence times for the vernier pairs and a corresponding total number of light pulses to each occurrence time, means for utilizing the occurrence times to fit an occurrence function of total number of light pulses versus time, and means for correlating the non-vernier signals to the occurrence function so as to effect a plot of the non-vernier signals versus pulse period as a measure of linearity of the photodetector.

In a preferred embodiment the means for directing a train of light pulses comprises a light source for emitting a stable light beam, and a disk disposed in the light beam. The disk has a slot therein with a selected slot width so that upon rotation the disk passes the light pulses to the photodetector. The means for smoothly changing the pulse period comprises means for rotating the disk at smoothly changing speed, preferably by initially driving the disk to greater than the maximum rotational speed and freeing the disk to coast from the maximum rotational speed to the minimum rotational speed.

BRIEF DESCRIPTION OF THE DRAWINGS

FIG. 8b is a pair of plots of the derivative and the reciprocal thereof of the curve of FIG. 8a.

DETAILED DESCRIPTION OF THE INVENTION

Figure 1:
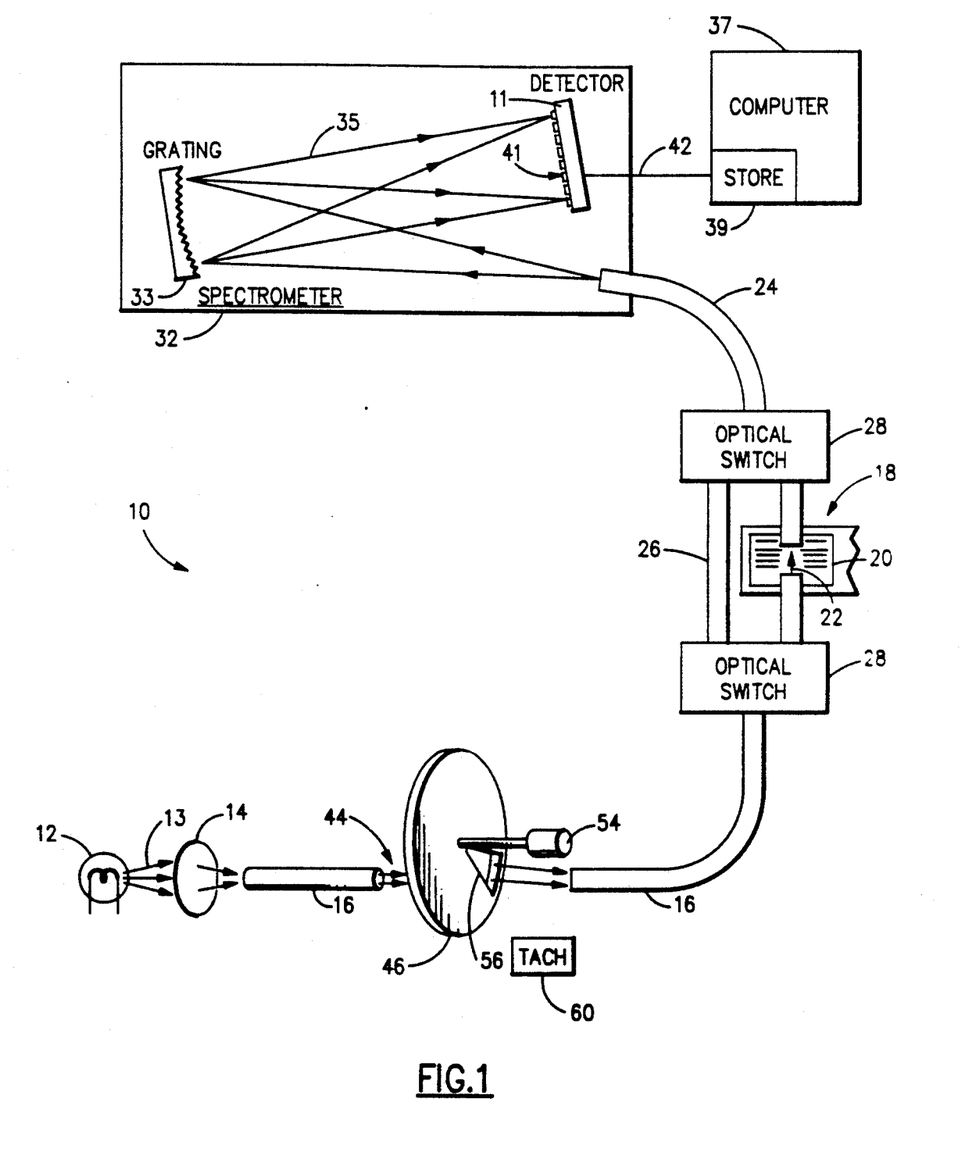
FIG. 1 is a schematic drawing of a spectrographic system incorporating the invention.

FIG. 1 illustrates a typical photometric instrument 10 having a photodetector 11 for which calibration of linearity with respect to amplitude of light is to be effected according to the present invention. A typical instrument may be, for example, a spectrographic polychromator or chemometric instrument requiring high sensitivity in the near infrared for measuring subtle changes in octane of gasoline. A stable but otherwise ordinary light source 12 provides light 13 that passes through a collimating lens 14 focused on an input end of an optical fiber 16. The fiber directs the light to a probe assembly 18 immersed in a liquid such as the gasoline to be tested. The probe may be of the type disclosed in co-pending U.S. patent application Ser. No. 773,189 filed Oct. 8, 1991 (Hoult) and may include optics not shown herein for simplicity. Although shown as a straight-through probe, the probe instead may have folding optics with reflectors to return light back into return paths in a bundle of optical fibers.

In the probe a sample space 20 is provided for the liquid so that the light 22 is passed through the liquid, where some of the light may be filtered selectively. The filtered light is picked up by a second optical fiber 24. A bypass fiber 26 with optical switching 28 is provided for selectively bypassing the liquid with the light through the fibers, to provide a standard with which to compare the filtered light. The second fiber 24 carries the light to a spectrometer 32 utilizing, for example, a concave grating 33, which disperses the light 35 to the detector 11. Signals from the detector representing the spectrum are directed into a computer 37 for storing 39 and processing. In the present example, the spectrum is used as a "fingerprint" of the sample liquid.

Figure 2:
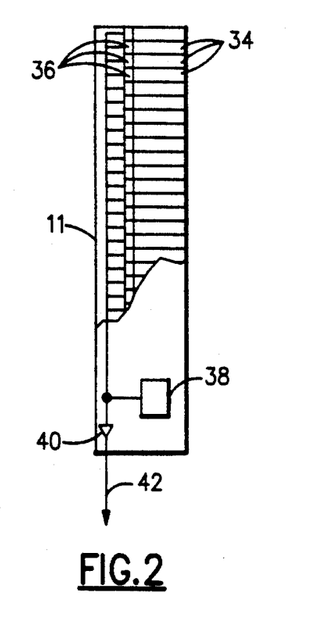
FIG. 2 is a simplified drawing of a photodetector component of the system of FIG. 1.

The photodetector 11 (FIG. 2) is a conventional solid state type such as RL1024S produced by EG&G Reticon. Such a detector typically is a self-scanned photodiode array or a charge coupled device, or may be a charge injection device, or the like. This has a linear array of adjacent photosensitive pixel areas 34, for example 1024 such pixels. Incident light on an area causes a buildup of charge which is read out periodically through gates 36 when the area is also cleared to begin a new charge buildup. Using integrated circuitry including a clock 38 and amplifier 40 in the device, the pixels are read out sequentially to produce voltage signals fed through a line 42 to the computer 37 (FIG. 1). Each signal represents the amount of light received by a selected pixel during a readout interval, i.e. the period between readouts. The amount of light received is the total number of photons, alternatively described as the detected light intensity integrated over the interval. The readout period also generally is the cycle time of readouts over the entire array of pixels. This period may be selected according to light levels so as to obtain a suitable operational range, for example between 10 and 100 milliseconds.

The present purpose is to determine linearity of the detector 11 including its integrated circuitry and any other associated circuitry in the instrument including analog/digital converters in the computer 33. The questioned linearity is with regard to the magnitudes of the readout signals representing different amounts of light.

According to the invention, a gap 44 is provided in one of the fibers for inserting a rotating disk 46. As shown, the disk is in a gap in the first fiber 16, but the actual location is not important, as long as it is between the light source and the detector. The steps herein ordinarily should be carried out with no liquid in the probe, or with the bypass in place, but the method could be effected with liquid in place.

Figure 3:
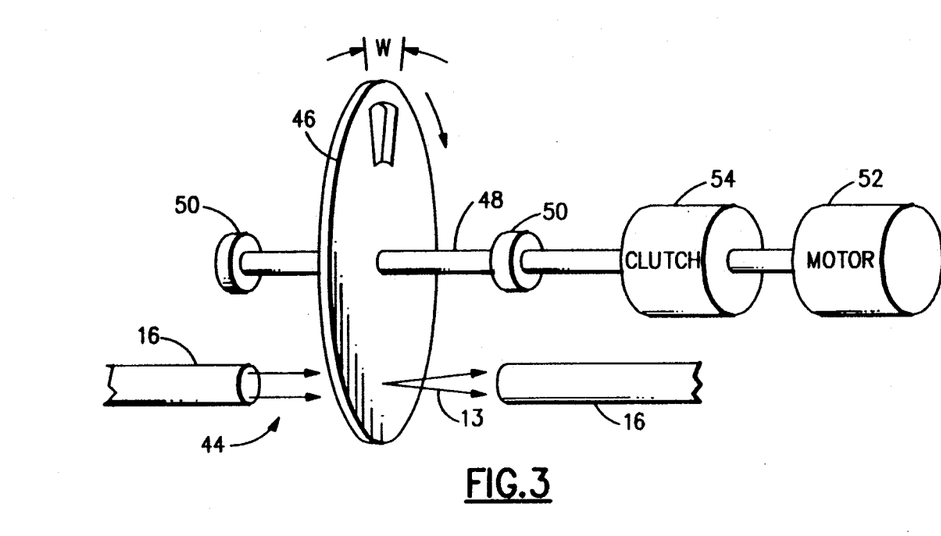
FIG. 3 is a drawing of a rotating disk component of the system of FIG. 1.

FIG. 3 shows the gap 44 and disk 46 in more detail. The disk has an axle 48 mounted on bearings 50, and the disk is driven by a motor 52 through a clutch 54 that can release the disk from the motor. The disk has at least one slot 56 that is passed through the light beam 13. The invention is described herein for one slot, but two or more may be useful, with suitable accounting taken in the computations. Either the fiber ends at the gap are very close together (FIG. 1) with the disk between them or, as shown in FIG. 3, preferably a pair of lenses 58 are placed in series with conjugate foci respectively at the fiber ends and the disk.

The disk 46 advantageously is operated by driving it with the motor 52 to a speed above a selected maximum rotational speed, and releasing the clutch 54 to allow free running of the disk to coast from the maximum rotational speed to the minimum rotational speed. An optically sensing tachometer 60 (FIG. 1) may be used to measure speed so as to signal the computer to take data during these extremes. With good bearings 50 and a relatively heavy disk (e.g. 25 cm diameter and 2.5 Kg mass), the disk will decrease very smoothly in speed through the selected range. Alternatively the disk may be driven with a very smooth variable speed motor over the range. It is not necessary to decrease speed; the speed may be smoothly increased or even cycled. However the preferred method with the clutch is quite simple and especially suitable for producing a ranging of speed without requiring a smoothly running motor.

While the disk is coasting down in speed and periodically passing the slot through the beam, continuous readouts are taken for at least one pixel on the detector. Voltage signals from the detector, representing the amount of light passed by the slot, versus the time of each readout, are stored in the computer after appropriate analog to digital conversion. The slot has a selected angular width W which is an angular fraction of the disk circle, the fraction being the ratio of angular width to 360°.

Figure 4A:
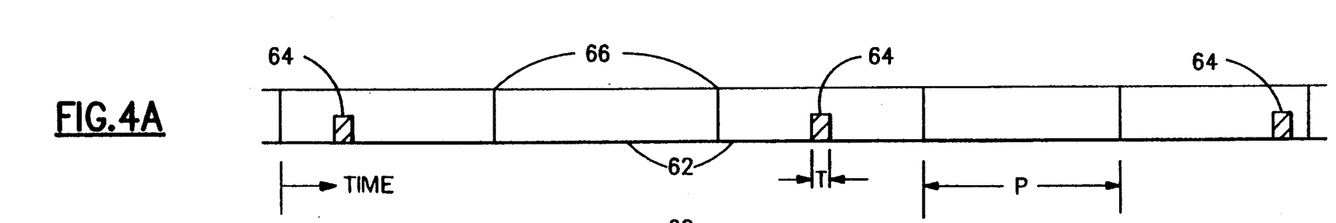
FIGS. 4a, 4b and 5 are schematic illustrations of sequential light pulses effected by the disk and superimposed readout intervals of the photodetector of FIG. 2.
Figure 4B:
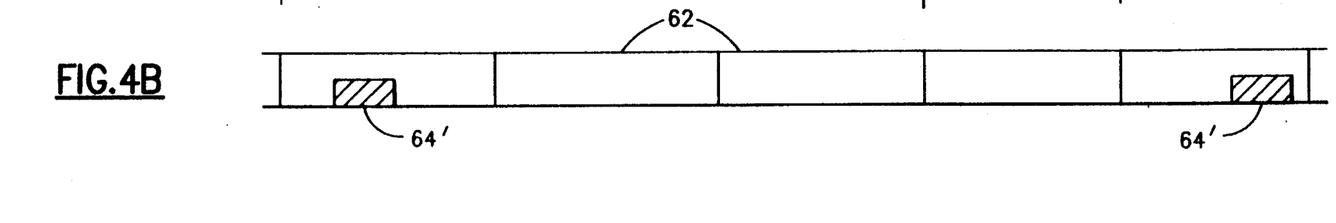

FIG. 4a shows readout intervals 62, each being equal to a predetermined readout period P for the detector set through the computer. Superimposed thereon are the timings 64 for light pulses. The actual timings of the pulses shown in the plot are unknown, as the pulses are read out at the end 66 of each interval. However, the pulse time width T, which is proportional to the stored signal because of the stability of the light source, is effectively determined by the slit width and the rate of spin of the disk. FIG. 4b shows the pulses 64' when the disk is spinning at slower speed. The pulses are longer and proportionately further spaced.

For reasons that will become clear below, a necessary restriction is that pulses 64,64' not fall within adjacent intervals, i.e. the pulses must occur no more often than every other interval as shown in FIG. 4a. Therefore, the maximum rotational speed of the disk must not be greater than half of the reciprocal of the readout period P. Also, the minimum rotational speed and the width W of the slot are selected cooperatively so that no pulse duration T is longer than the readout period P.

Figure 5:
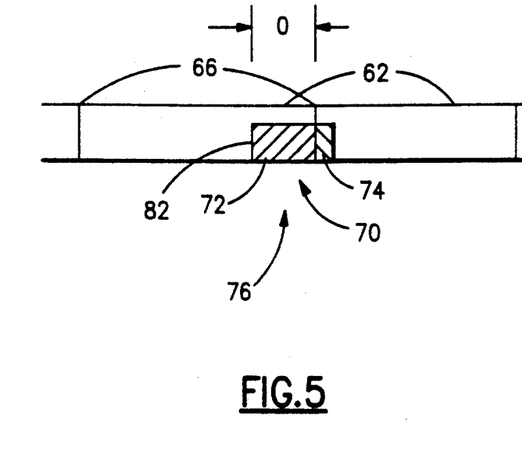

Occasionally a light pulse 70 will straddle two readout intervals 62 as shown in FIG. 5. With parallel reference to a flowchart (FIG. 6), after starting (110) and reading of stored signals versus time (112), the straddles are recognized and identified (114) in a computer program as two adjacent readouts 72,74. Such adjacent readouts are always straddles because of the above-described constraint on maximum rotational speed. These adjacent readouts are used for computing disk speed and, therefore, are herein termed vernier pairs 76 of signals. The others, excluding the vernier pairs, are termed non-vernier signals (e.g. signals 64 and 64' in FIGS. 4a and 4b) and a set of these is also established (116) by the computer program.

Initially (before step 114), a plot or count is made (118), within the computer program, of all readout signal occurrences versus time, in order to provide a count of number of disk rotations versus time from the starting point (viz. at the maximum selected speed). For illustration (FIG. 7), the non-verniers 64 are shown as short horizontal lines representing the uncertainty of pulse time within the readout intervals. For the vernier pairs 76 only the first signal 72 (FIG. 5) of each pair is plotted, as the second 74 is for the same light pulse readout. These vernier signal times are the actual readout times with an accuracy of pulse width and so are better known and are plotted as points. The initial plot including non-verniers 64 establishes (120) a count for the rotation number for each vernier pair 76, the role of the non-verniers in this plot being to provide the full count.

Precision occurrence times for the vernier pairs are then ascertained (122). Utilizing times of readout only for the vernier pairs, a preliminary function represented by curve 78 (FIG. 7) is fitted (124) (FIG. 6) for number of occurrences, viz. passages of the slot through the light beam versus time, representing number of disk rotations R (revolutions) versus time T, the counts and time commencing at the starting point. A preliminary occurrence time (126) for the pair and a preliminary time period (128) of one full disk rotation at the occurrence time are determined. The preliminary occurrence time may be the actual stored readout time of the first signal of the pair, within the present purview, but an estimate taken from the preliminary fitted curve is more accurate. A vernier fraction is defined (130) as the ratio of one, e.g. first, signal in the pair to the total magnitude of the two signals in the pair added together.

To improve the accuracy of estimating the start time of the vernier pulse, a time offset (132) is calculated. A smooth curve is fitted to the preliminary occurrenced time data. The slope at the vernier points is an estimate of the rotational speed of the disk. The reciprocal of this slope is then the estimated time for rotation (128) of the entire disk. The multiplication product of this time and the angular fraction (of the slot to the disk circle) is the estimated time for an entire pulse. By forming a multiplication product of this number with the vernier fraction, an estimate of the start time of the pulse is obtained (134).

Figure 7:
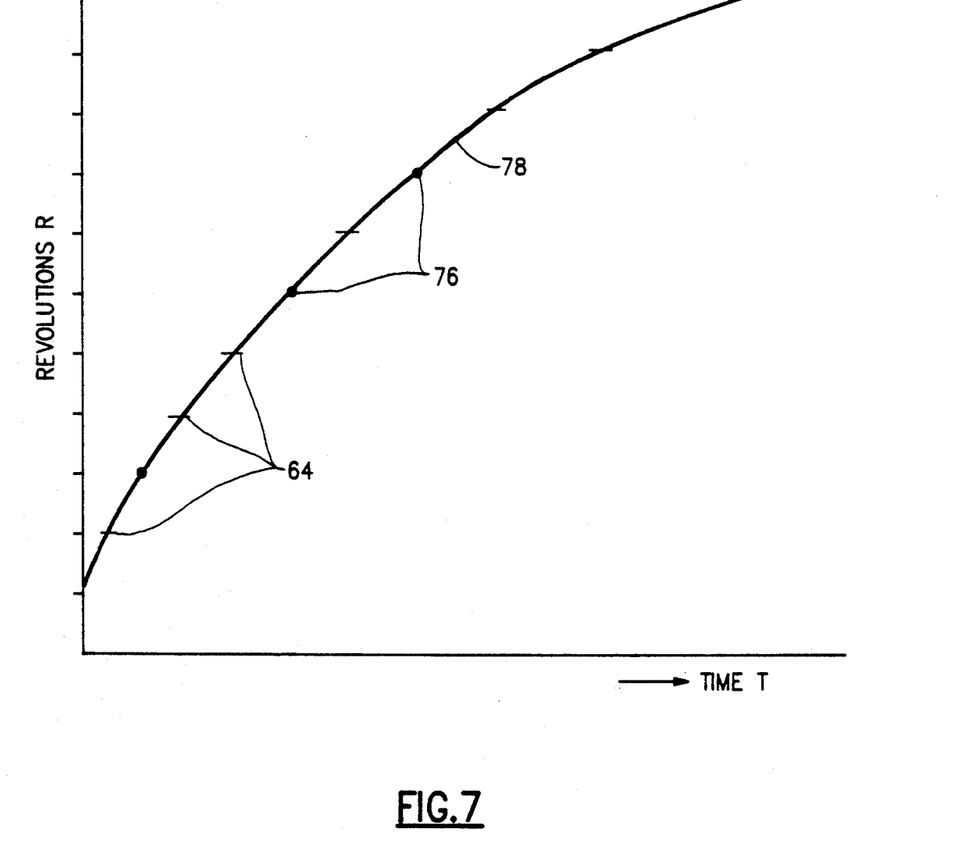
FIG. 7 is plot of illustrative readouts from the photodetector of FIG. 2, and a preliminary curve thereof, plotted as disk revolutions versus time.
Figure 8A:
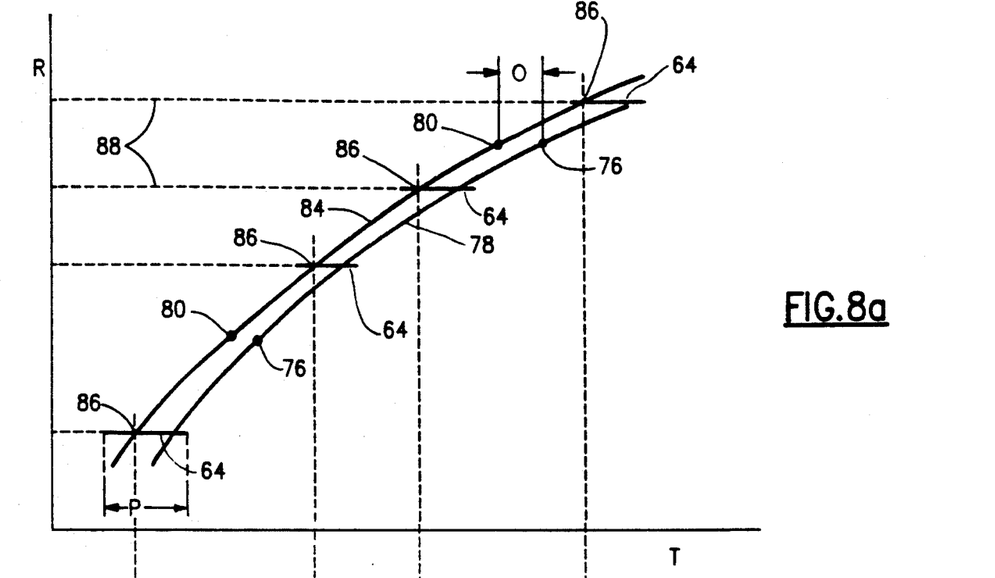
FIG. 8a is a detail of FIG. 7 further showing corrected readout occurrence times and a fitted curve thereto.

The occurrence time of the vernier pair is corrected (134) by the time offset. FIG. 8a includes a detailed portion of the plot of FIG. 7, showing initial plots of verniers 76, non verniers 64 and the preliminary curve 78. The corrected occurrence times 80 for the verniers are shown displaced by the calculated time offset O, which will shift the curve by amounts that vary for each vernier.

It is convenient to correct to a start time 82 (FIG. 5) of each light pulse, although some other point could be used such as end time or center point. In the case of start time, the time offset is subtracted from the preliminary occurrence time. This will shift the curve to the left. In any event, the corrected occurrence times for the vernier pairs are utilized to fit (136) (FIG. 6) a corrected function or curve 84 (FIG. 8a) representing number of disk rotations R versus time. The functional curve fitting should be done accurately, preferably with the conventional cubic spline method, although an exponential decay curve may be sufficient.

The corrected occurrence time may be sufficiently accurate for proceeding (137). However if desired the foregoing steps of computing parameters and fitting the corrected function may be iterated (138) at least once to improve accuracy for the final corrected occurrence function (136).

From the final corrected functional curve 84, a point of time 86 is determined (140) for the number of disk rotations for each of the non-vernier signals. These points of time 86 now precisely locate the non-vernier signals 64 in time, which previously were uncertain within the readout period P.

Figure 8B:
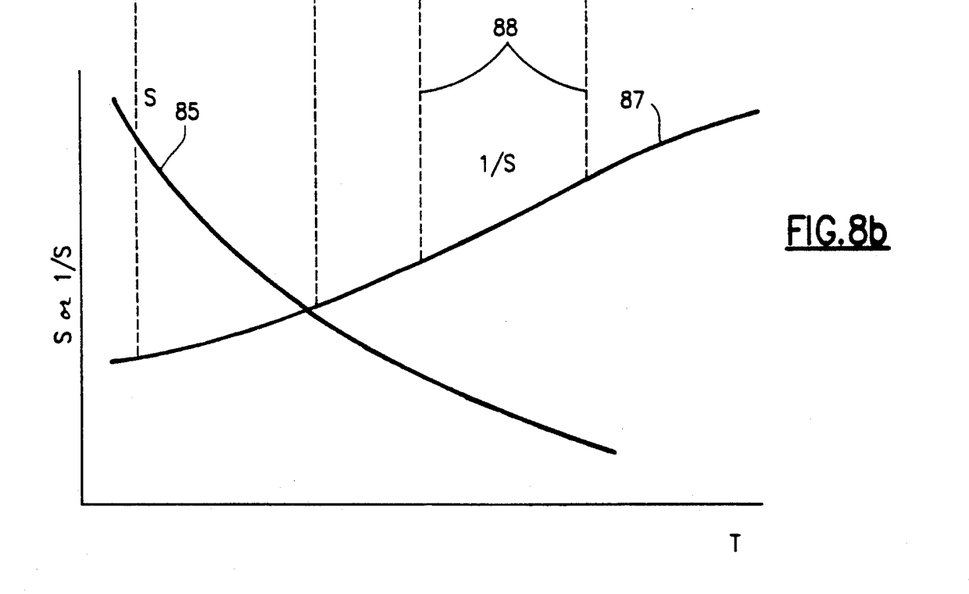
Figure 9:
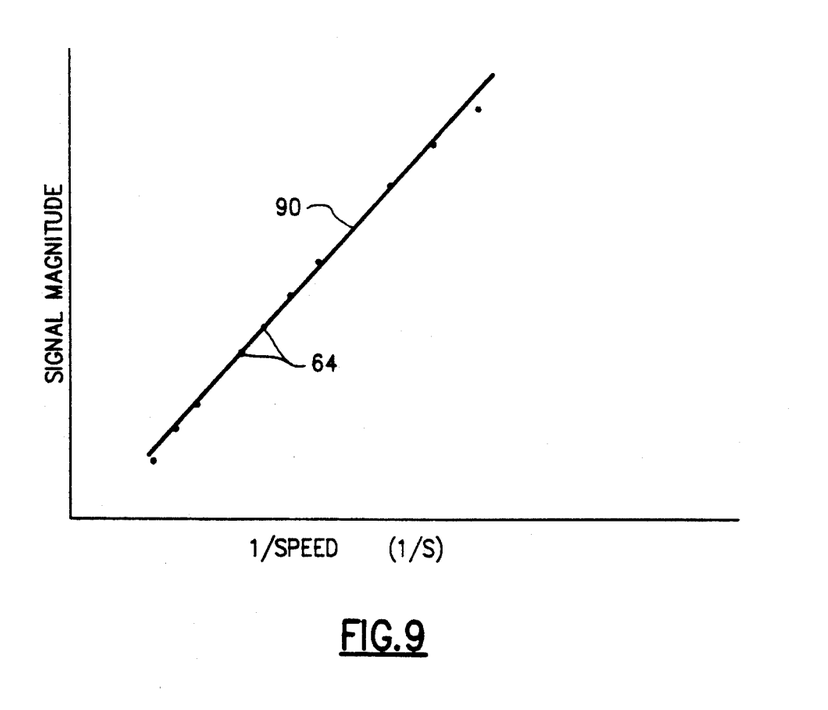
FIG. 9 is a plot of signals from the photodetector versus the reciprocal derivative derived from FIGS. 8a and 8b, representing linearity of the photodetector.

The remaining steps and means 139 utilize the points of time to calibrate linearity of the photodetector 11 by correlating the non-vernier signals to the occurrence function so as to effect a correlation function versus pulse period. A computation of the derivative 85 (FIG. 8b) of the corrected curve 84 of R versus time represents rotational speed S of the disk versus time, and a further curve 87 (FIG. 8b) is computed (142) representing reciprocal of rotational speed (1/S) versus time, which is the same as pulse period versus time. The points of time 86 for the non-vernier signals are used to identify (e.g. via broken lines 88) corresponding points for reciprocal of rotational speed (1/S) on the further curve. With this curve and further identification of the points with magnitudes of signals, a plot 90 of a correlation function is made (144) of the non-vernier signals versus reciprocal of rotational speed (FIG. 9), i.e., versus pulse period. For clarity, the foregoing steps are illustrated with respect to plotted curves 85,87; ordinarily, the computer program will handle these functionally.

The latter plot (correlation function) should be at least approximately linear, and serves as a calibration of linearity of the photodetector. It may be used in any of several ways, for example by allowing selection of a linear range of integrated light intensities in applications, or by providing correction factors to measurements.

The correction factors may be in the form of regression coefficients.

Figure 6:
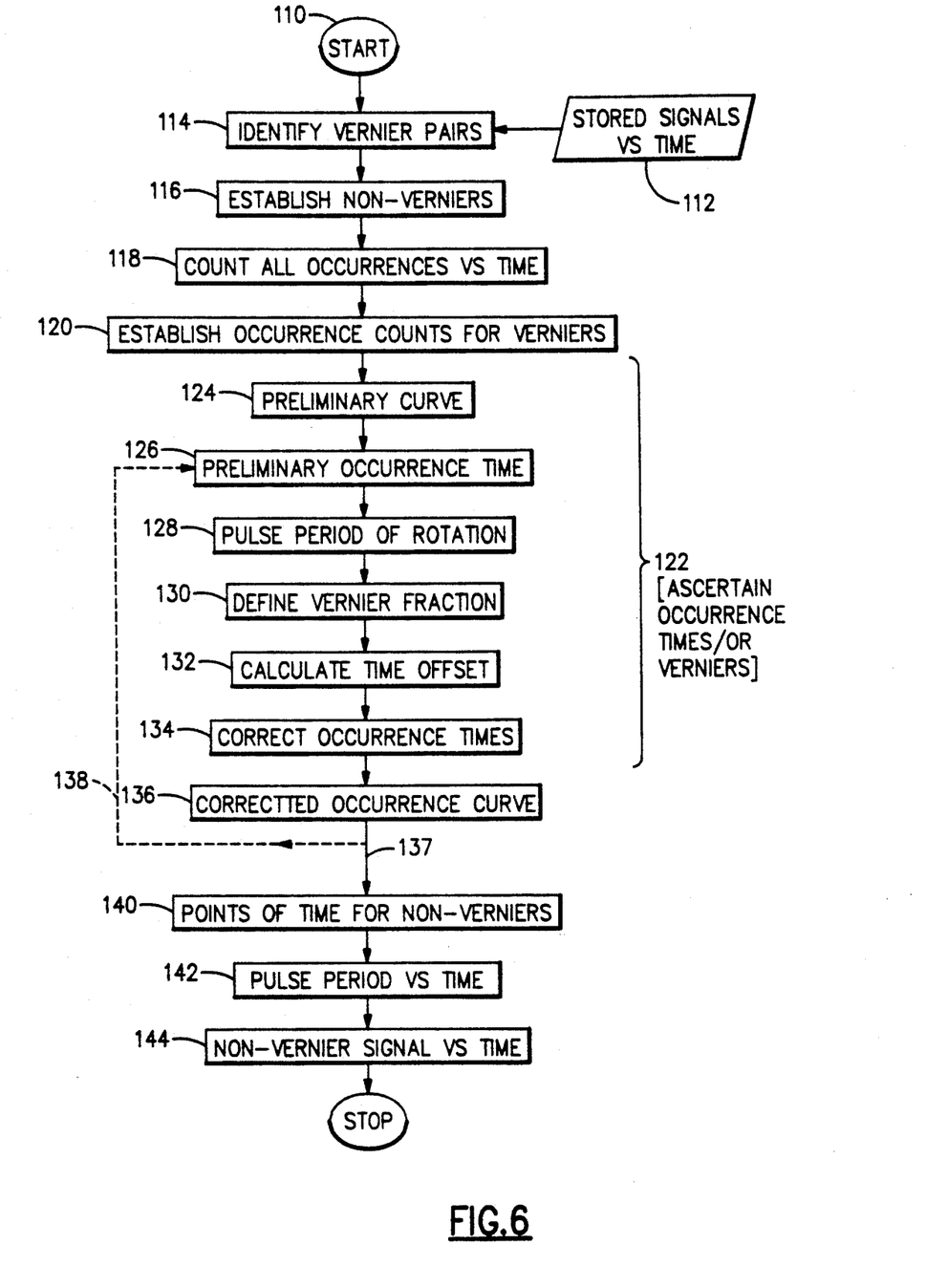
FIG. 6 is a flowchart for a computer program utilized in the invention.

For further accuracy readouts for a number of the pixels may be taken and pooled for the above-described determinations. For example ten pixels may be useful, selected from across the detector. Too many may slow computations too much. As there are time differences in the readouts among the selected pixels, the readout times should be corrected for these differences from step 112 in the flow chart (FIG. 6). The time shifts would be in proportion to positions of the pixels in the array. The frequency of occurrences of verniers would increase in proportion to the number of pixels used, for example 10 times if 10 pixels are used.

Furthermore, use of multiple pixels enables an alternate way of calculating the time offset (132). When two or more pixels have verniers corresponding to the same pass of the slot through the beam, their vernier fractions (130) will differ because of the known shift time in the readout. This shift time changes by addition or subtraction the start time of the pulse in a given pixel, depending on whether that pixel is read out later or earlier than a reference one. Knowledge of this shift time along with measurement of the vernier fractions enables a direct computation of the pulse width. When many pixels are chosen, this computation may most accurately be performed by plotting the verniers from all the useable pixels.

The programming means for carrying out the foregoing steps, as outlined by the flowchart of FIG. 6, is conveniently and readily achieved with a conventional computer system such as "C" generally available through the supplier of the operating system utilized with the computer. Curve fitting is conventional and programs are readily available. The program may be compiled, for example, on a Digital Equipment Corporation Model 316 SX computer associated with the spectrometer.

It should be understood that some of the computational steps described herein and in the claims may be combined into one formula which is to be considered equivalent to such series of steps. Also, steps of "plotting" referenced herein may be achieved within a program and not necessarily in visual form.

In an example of selected parameters for a 25 cm disk, the readout period is 10 milliseconds and the angular width of the disk slot is 1.8° the latter being an angular fraction of 1.8/360=0.005. According to the forgoing rules, the maximum disk speed is not greater than 3000 revolutions per minute (RPM), and the minimum speed is not less than 30 RPM, to achieve a dynamic range of 100:1 in the linearity test.

The invention has been described with respect to a spectrometric instrument, specifically of the type used for precision measurements of optical absorption in liquids or semi-transparent solids. However, the invention is broadly directed to calibrating a photodetector of the type having periodic readouts. Therefore, it will be appreciated that the invention may be utilized with any photometric instrument incorporating such a detector, such as for atomic emission spectroscopy, atomic absorption spectroscopy or astronomy; or for a non-spectrographic instrument such as a camera; or simply for calibrating detectors before putting them to use.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

We claim:

1. A method of determining linearity of a photodetector having sequential readouts of signals, each signal correlating with amount of light received during a corresponding readout interval, each readout having a time of readout, and all readout intervals being equal to a predetermined readout period, the method comprising:

directing a train of light pulses to the photodetector, the light pulses having equal intensity and a variable pulse period between successive pulses, and each light pulse having a variable pulse width equal to a constant fraction of pulse period:

selecting the constant fraction and a maximum pulse period cooperatively so that each pulse width is not greater than the readout period, and further selecting a minimum pulse period not less than two times the readout period;

smoothly changing the pulse period between the maximum pulse period and the minimum pulse period, while reading out and storing sequential signals from the photodetector and corresponding times of readout;

identifying a set of vernier pairs of signals as those pairs of signals occurring in adjacent readout intervals, and establishing a set of non-vernier signals excluding the vernier pairs;

ascertaining occurrence times for the vernier pairs and a corresponding total number of light pulses to each occurrence time;

utilizing the occurrence times to fit an occurrence function of total number of light pulses versus time; and correlating the non-vernier signals to the occurrence function so as to effect a correlation function of the non-vernier signals versus pulse period as a measure of linearity of the photodetector.

2. The method of claim 1 wherein the step of correlating comprises determining from the occurrence function point of time for the non-vernier signals, computing from the occurrence function a further function representative of pulse period versus time, identifying from the further function a corresponding pulse period for each point of time and thereby for each corresponding non-vernier signal, and effecting the correlation function with the non-vernier signals versus corresponding pulse period.

3. The method of claim 1 wherein the step of ascertaining occurrence times comprises:

fitting a preliminary function of number of light pulses versus times of readout of firstly occurring signals of the vernier pairs;

computing occurrence times for each vernier pair by determining from the preliminary function a preliminary occurrence time for the pair and a preliminary pulse period at the preliminary occurrence time, defining a vernier fraction as the ratio of one signal in the pair to a sum of signals constituting the pair, and calculating a time offset as a product of the vernier fraction and the constant fraction and the preliminary period; and correcting the preliminary occurrence time with the time offset, thereby generating a set of corrected occurrence times.

4. The method of claim 3 further comprising iterating at least once the steps of computing occurrence times, by initially utilizing a previously fitted occurrence function as a new preliminary function.

5. The method of claim 1 wherein the step of directing a train of light pulses comprises disposing in a stable light beam a rotating disk having a slot therein with a selected slot width so as to pass the light pulses to the photodetector, and the step of smoothly changing the pulse period comprises rotating the disk at smoothly changing speed.

6. The method of claim 5 wherein the step of rotating is effected by initially driving the disk to greater than the maximum rotational speed, and freeing the disk to coast from the maximum rotational speed to the minimum rotational speed.

7. The method of claim 1 wherein the photodetector is disposed in a spectrophotometer that includes dispersion means receptive of the light pulses so as to direct spectrally dispersed light pulses to the photodetector.

8. The method of claim 7 wherein the photodetector comprises a plurality of photosensitive pixels each receptive of a different spectral portion of the dispersed light pulses, and the method further comprises employing at least two of the pixels for producing the sequential signals.

9. The method of claim 8 wherein the step of utilizing the occurrence times includes correcting said times for differences thereof among the pixels.

10. A precision photometric instrument comprising:
a photodetector having sequential readouts of signals, each signal correlating with amount of light received during a corresponding readout interval, each readout having a time of readout, and all readout intervals being equal to a predetermined readout period;
light means for directing a train of light pulses to the photodetector, the light pulses having equal intensity and a variable pulse period between successive pulses, and each light pulse having a variable pulse width equal to a constant fraction of pulse period;
changing means for smoothly changing the pulse period between a maximum pulse period and a minimum pulse period as to effect a series of sequential signals, the minimum pulse period being not less than two times the readout period, and the maximum pulse period and the constant fraction cooperatively being such that each pulse width is not greater than the readout period;
storing means for storing sequential signals from the photodetector and corresponding times of readout;
means for identifying a set of vernier pairs of signals as those pairs of signals occurring in adjacent readout intervals, and establishing a set of non-vernier signals excluding the vernier pairs;
means for ascertaining occurrence times for the vernier pairs and a corresponding total number of light pulses to each occurrence time;
means for utilizing the occurrence times to fit an occurrence function of total number of light pulses versus time; and
means for correlating the non-vernier signals to the occurrence function so as to effect a correlation function of the non-vernier signals versus pulse period as a measure of linearity of the photodetector.

11. The instrument of claim 10 wherein the means for correlating comprises means for determining from the occurrence function points of time for the non-vernier signals, means for computing from the occurrence function a further function representative of pulse period versus time, means for identifying from the further function a corresponding pulse period for each point of time and thereby for each corresponding non-vernier signal, and means for effecting the correlation function with the non-vernier signals versus corresponding pulse period.

12. The instrument of claim 10 wherein the means for ascertaining occurrence times comprises means for fitting a preliminary function of total number of light pulses versus times of readout of firstly occurring signals of the vernier pairs, means for determining from the preliminary function a preliminary occurrence time for the pair and a pulse period at the preliminary occurrence time, means for defining a vernier fraction as the ratio of one signal in the pair to a sum of signals constituting the pair, means for calculating a time offset as a product of the vernier fraction and the constant fraction and the pulse period, and means for correcting the preliminary occurrence time with the time offset.

13. The instrument of claim 10 wherein the means for directing a train of light pulses comprises a light source for emitting a stable light beam, and a disk disposed in the light beam and having a slot therein with a selected slot width so that upon rotation the disk passes the light pulses to the photodetector, and the means for smoothly changing the pulse period comprises means for rotating the disk at smoothly changing speed.

14. The instrument of claim 13 wherein the means for rotating comprises means for initially driving the disk to greater than the maximum rotational speed, and means for freeing the disk to coast from the maximum rotational speed to the minimum rotational speed.

15. The instrument of 10 wherein the photodetector is disposed in a spectrophotometer that includes dispersion means receptive of the light pulses so as to direct spectrally dispersed light pulses to the photodetector.

16. The instrument of claim 15 wherein the photodetector comprises a plurality of photosensitive pixels each receptive of a different spectral portion of the dispersed light pulses, and the selected signals include signals from at least two of the pixels.

17. The instrument of claim 16 wherein the means for utilizing the occurrence times includes means for correcting said times for differences thereof among the pixels.

* * * * *